United States Patent [19]
Imai

[11] Patent Number: 5,891,632
[45] Date of Patent: Apr. 6, 1999

[54] METHOD AND DEVICE FOR FRAGMENT TRACE DATA DISPLAY IN DNA BASE SEQUENCING

[75] Inventor: Kensaku Imai, Kawasaki, Japan

[73] Assignee: Fujitsu Limited, Kawasaki, Japan

[21] Appl. No.: 685,959

[22] Filed: Jul. 22, 1996

[30] Foreign Application Priority Data

Jul. 27, 1995 [JP] Japan ................................. 7-192006

[51] Int. Cl.$^6$ ..................................................... C12Q 1/68
[52] U.S. Cl. .............................. 435/6; 382/129; 382/191; 382/294; 345/438; 345/439; 345/442
[58] Field of Search ................................ 435/6; 364/130; 360/97.01; 382/129, 191, 294; 345/438, 439, 442

[56] References Cited

PUBLICATIONS

Kerlavage, et al., Proceedings of the Twenty–sixth Annual Hawaii International Conference on System Sciences, 1993.
Lipshutz, et al. "DNA Sequence Confidence Estimation", *Genomics*, vol. 19, pp. 471–424 (1994).
Gleeson, et al. "A Trace Display And Editing Program for Data From Fluroescence Based Sequencing Machines", *Nucleic Acids Research*, vol. 19, No. 23, pp. 6481–6483 (1991).
T. Wakasugi, "Protein Nucleic Acid Enzyme", No. 11, vol. 39 (Aug. 5, 1994), pp. 1780–1777.
B. Alberts, et al., "Molecule Biology of Cell" (Jun. 10, 1987), pp. 185–190.
J. D. Watson, et al., "Molecule Biology of a Gene" (Sep. 9, 1988), pp. 240–281.
Dear et al. Nucleic Acid Research. vol. 19, No. 14, pp. 3907–3911, Jul. 25, 1991.

*Primary Examiner*—James Ketter
*Assistant Examiner*—Irem Yucel
*Attorney, Agent, or Firm*—Staas & Halsey

[57] ABSTRACT

In a DNA base sequencing, a consensus sequence is obtained by linking a plurality of DNA fragments obtained by a DNA sequencer, and a base sequence to be edited is determined in the consensus sequence. Then, a trace corresponding to the determined base sequence to be edited is identified among traces obtained by the DNA sequencer. The identified trace is displayed in correspondence with the base sequence to be edited. At this time, the base sequence to be edited is displayed so that an interval between bases becomes even.

8 Claims, 15 Drawing Sheets

| TRACE DATA | | | | | |
|---|---|---|---|---|---|
| X | 1 | 2 | 3 | 4 | 5 . . . . . 10000 |
| A | | | | | |
| T | | | | | |
| G | | | | | |
| C | | | | | |

16 BITS

FIG. 6

| n | 1 | 2 | 3 | . | . | . | . | . | 400 |
|---|---|---|---|---|---|---|---|---|-----|
| BC | A | T | C | | | | | | |
| X | 12 | 130 | 250 | | | | | | |

ORIGINAL BASE SEQUENCE DATA

FIG. 7

METHOD AND DEVICE FOR FRAGMENT TRACE DATA DISPLAY IN DNA BASE SEQUENCING

BACKGROUND OF THE INVENTION

1. Field of the Invention

The present invention relates to a method for determining a base sequence of a DNA which is one type of nucleic acid, and more particularly to a method for displaying a base sequence trace (waveform) of a DNA fragment for use in a DNA base sequencing using a DNA sequencer.

2. Description of the Related Art

A constituent of a nucleic acid is a nucleotide, which is composed of a base, pentose, and phosphoric acid. The phosphoric acid and a nucleoside combine to form the nucleotide. Nucleosides are cross-linked by the phosphoric acid, so that a DNA (deoxyribonucleic acid) and an RNA (ribonucleic acid), which are polymers, are generated.

The base forming the nucleic acid comprises two types, a purine and a pyrimidine. The purine comprises an adenine A and a guanine G, while the pyrimidine comprises a cytosine C and a thymine T.

The DNA has a polynucleotide-chain structure, in which adenine A, guanine G, cytosine C, and thymine T are aligned as a string. If DNAs were extracted from one chromosome of a human cell and linked in sequence, they would extend for about one meter, in which three billion bases remain in sequence.

Accordingly, determining a sequence of the four bases adenine A, guanine G, cytosine C, and the thymine T allows genetic information to be analyzed. The DNA sequencing technology for determining a base sequence progresses as techniques in other fields advance. Its progress correlates closely to progress made in technical fields such as the discoveries of restriction enzymes and enzymes related to nucleic acid, DNA cloning, nucleo-chemistry, etc.

In recent years, computer technology is frequently applied to the DNA sequencing. Since the computer technology enables accumulation and entry of huge amounts of data beyond the capability of a human being, a computer is used as an essential tool for determining a base sequence.

As described above, the DNA has a structure of a primary base sequence linked in the form of a chain. The DNA chain has directionality. That is, a base sequence ATGCACGA→ is different from a base sequence ATGCACGA← (that is, AGCACGTA→).

Both ends of the DNA chains are named. The end where a hydroxyl group is linked to a sugar at a location 3' is called the 3' end, while the other end where a phosphoric acid group is linked to a sugar at a location 5' is called the 5' end. Normally, a DNA chain is described so that the 5' and 3' ends are arranged at the left and right sides respectively.

The DNA exists in a double-stranded state where two complementary base sequences in different directions are united. There is a definite relationship between the two complementary base sequences which face each other. That is, the adenine A only faces the thymine T, while the guanine G only faces the cytosine C. An example of a double-stranded DNA is given below.

ATGCATGCTAGCTAGCT→("a" strand)

TACGTACGATCGATCGA←("b" strand)

As shown above, the "a" strand pairs with the "b" strand. The "b" strand is complementary to the "a" strand. Accordingly, the "b" strand can be also represented as follows:

AGCTAGCTAGCATGCAT→

The DNA is genetically defined by making a pair of two complementary base sequences. If one of the two complementary base sequences is determined, the other of the two can be determined. This means that the base sequence of the DNA can be determined.

For a DNA sequencer for automatically reading a base sequence of a DNA, the dideoxyn method or the Sanger method is used to determine a base sequence. Normally, when DNA synthesis is performed using a portion of one of the complementary double strands of a DNA as a primer for initiating the DNA synthesis, adding a dideoxynucleotide halts the DNA synthesis. As a result, fragments of the DNA having a variety of lengths can be obtained. Therefore, by adding the dideoxynucleotide corresponding to each of the bases G, A, T, and C at the time of DNA synthetic reaction, the DNA fragments having a variety of lengths whose chains are cleaved at each location of each of the bases, can be obtained.

FIG. 1 is a schematic diagram showing a process for generating DNA fragments cleaved at locations of one particular nucleotide, the adenine A in this case. As shown in this figure, the chemical process for removing one nucleotide, that is, the adenine A from a DNA 1 whose 5' end is labelled with $^{32}p$, is performed. As a result, the DNA 1 is separated into radioactive labelled fragment 2 having a phosphoric acid group at the 5' end on the left side of the figure and fragments 3 which are non-labelled. Then, these fragments are isolated by gel electrophoresis. The radioactive fragments 2 are detected at locations respectively corresponding to the lengths of the fragments (or molecular weights) by autoradiography.

With the DNA sequencer, DNA fragments generated by a reaction of the dideoxyn method are fluorescence-marked. The DNA fragments having a variety of lengths of fluorescence-marked chains are isolated by a gel electrophoresis. For the DNA fragments electrophoresed in a gel, their fluorescent pigment is excitation-radiated at a certain location on the gel by laser irradiation, and detected by an optical detector. By detecting the fluorescence continuously and simultaneously with the electrophoresis, data of the electrophoretic patterns of DNA fragments corresponding to each of the bases G, A, T, and C, can be obtained. The data thus obtained is analyzed by a computer, and converted into base sequence data.

Output data from the DNA sequencer includes a DNA base sequence itself, and trace data (waveform data) used to determine a base sequence. The trace data corresponds to data of a gel electrophoretic pattern, and a location of a peak in each of the traces (waveforms) of the bases G, A, T, and C corresponds to a location where a corresponding base exists.

However, since the number of bases included in a base sequence of a DNA is generally very large, it is difficult to determine the whole of the base sequence at one time using the DNA sequencer. Accordingly, by separating a DNA to be determined into a plurality of fragments, determining a base sequence of each of the plurality of fragments, and linking the base sequences, the entire base sequence is determined. For the fragmentation, the DNA is fragmented by overlapping both ends of each of the fragments, and a base sequence of each of the fragments is obtained.

For the process for determining a base sequence using the DNA sequencer, the number of bases read at one time is limited, as described above. Furthermore, the contents of read sequence data may be quite ambiguous depending on the accuracy of experiments conducted by using gel electrophoresis.

FIG. 2 shows an output example of trace data obtained from a DNA sequencer. In each of the graphs shown in this figure, a vertical axis indicates fluorescent intensity, while numerical values on a horizontal axis indicate base numbers in a DNA sequence. Since traces can be enlarged for display depending on need as shown in the four graphs in this figure, the base sequence can be read corresponding to the peak locations of the respective traces in these graphs.

For a DNA whose base sequence is desired to be determined as described above, an editing operation such as enlarging a fragment sequence, linking fragment sequences, removing a base which is difficult to be identified, inserting a base, depending on need, etc., is performed to assemble a base sequence. In this case, it is desirable that the editing and assembling operations be performed more accurately and more quickly to obtain a desired base sequence.

When fragment data read by the DNA sequencer is linked or edited in order to assemble a base sequence, it is often the case that a character sequence is extracted from the data read by the sequencer to perform linking and editing operations, and at the same time, trace data is referenced, depending on need. Conventionally, only trace data corresponding to a fragment is displayed for referencing the trace data. Such a display does not enable a study by making a comparison between traces. As described above, peak intervals of trace data may differ depending on experimental data due to non-uniformity of quality of gels used in electrophoresis, slight differences in experimental conditions, etc. Therefore, as long as traces are simply displayed, there is a difficulty in finding visual correspondence between portions of traces to be compared, and the display is not helpful for accurately assembling a base sequence.

Furthermore, as a molecular weight of a base increases in gel electrophoresis, a travel distance of the base becomes shorter, in a conventional method. As a result, base intervals corresponding to a trace become irregular.

FIG. 3 shows a graph where such irregularities of base intervals exist. For example, the interval between base numbers 100 and 200 is different from that between base numbers 600 and 700 in this figure. That is, it indicates that the base intervals are not regular. Due to slight differences in experimental conditions, locations of traces corresponding to the same base number are different. Accordingly, with an editing operation using such a graph, a simple comparison between traces cannot easily be made.

SUMMARY OF THE INVENTION

The object of the present invention is to provide a method and a device for facilitating finding a correspondence between locations on traces (waveforms) to be compared, when trace data (waveform data) of respective fragments of a DNA are compared. Another object of the present invention is to determine a base sequence more accurately in a process for linking fragment data and an editing operation after linkage, according to the above described method and device.

The method according to the present invention is a fragment trace data display method for determining a base sequence of the DNA based on traces representing base sequences of the plurality of fragments of the DNA obtained by an electrophoresis. This method includes the steps of: determining the base sequences of the plurality of fragments as fragment base sequences; obtaining a consensus sequence by linking the fragment base sequences; displaying the traces in correspondence with the consensus sequence; and determining the base sequence of the DNA by referencing the displayed traces in correspondence with the consensus sequence and editing the consensus sequence. The traces and the fragment base sequences are obtained as outputs from a DNA sequencer for determining the base sequence of the DNA.

The fragment trace data display method may further include the steps of: providing location information indicating a location on a trace for a base included in a fragment base sequence; identifying bases included in a base sequence to be edited, having location information, and positioned at both ends of the base sequence to be edited; and displaying a corresponding trace between the identified bases positioned at both ends in correspondence with the consensus sequence.

The fragment trace data display method may additionally include the step of displaying the consensus sequence in correspondence with a displayed trace, so that an interval between contiguous bases (spaces between adjacent bases) in the displayed consensus sequence becomes even (regular).

The fragment trace data display method may further include the steps of: providing location information indicating a location on the trace for the base included in the fragment base sequence; identifying bases included in the fragment base sequence, having the location information, and positioned at both ends of the fragment sequence; and displaying a corresponding trace between the identified bases at both ends in correspondence with the consensus sequence.

When a type of a base included in the consensus sequence is determined, if a type of a base indicated by a base sequence of a first fragment among the fragment base sequences is different from that indicated by a base sequence of a second fragment among the fragment base sequences, a symbol indicating either of the two bases may be used for the base to be determined.

Another method according to the present invention is a method for determining a base sequence of a DNA based on base sequences of a plurality of fragments forming a portion of the DNA and traces representing the base sequences of the plurality of fragments, which are obtained by a DNA sequencer. This method includes the steps of: determining a consensus sequence by linking the base sequences of the plurality of fragments of the DNA obtained by the DNA sequencer; determining a base sequence to be edited in the consensus sequence; identifying a trace corresponding to the base sequence to be edited among traces obtained by the DNA sequencer; and displaying the identified trace in correspondence with the base sequence to be edited.

This method may further include the steps of: providing location data indicating a corresponding location on a trace for each of the bases included in the base sequences of the plurality of fragments of the DNA; identifying the bases included in the base sequence to be edited, having the location information, and positioned at both ends of the base sequence to be edited; and displaying a trace existing between the location data of the identified bases positioned at both ends in correspondence with the consensus sequence.

This method may additionally include the step of displaying the consensus sequence in correspondence with the displayed trace, so that an interval (spaces) between contiguous bases becomes even (regular). When a type of a base included in the consensus sequence is determined, if a type of a base indicated by a base sequence of a first fragment among the fragment base sequences is different from that indicated by a base sequence of a second fragment among the fragment base sequences, a symbol indicating either of the two bases may be used for the base.

A device according to the present invention is intended for determining a base sequence of a DNA based on base sequences of a plurality of fragments forming a portion of a DNA, and traces representing the base sequences of the plurality of fragments, which are obtained by a DNA sequencer. This device includes a pre-process unit for determining a consensus sequence by linking the base sequences of the plurality of fragments of the DNA obtained by the DNA sequencer, an editing data setting unit for determining a base sequence to be edited in the consensus sequence, a trace data setting unit for identifying a trace corresponding to the base sequence to be edited among traces obtained by the DNA sequencer, and a trace data display unit for displaying the identified trace in correspondence with the base sequence to be edited.

The pre-process unit may provide location data indicating a corresponding location on a trace for each of bases included in the base sequences of the plurality of fragments of the DNA, and the edition data setting unit may identify bases included in the base sequence to be edited, having the location information, and being positioned at both ends of the base sequence to be edited. The trace data display unit may display a trace existing between location data of the identified bases positioned at both ends in correspondence with the consensus sequence.

The trace data display unit may display the consensus sequence in correspondence with a displayed trace, so that an interval (spaces) between contiguous bases becomes even (regular).

When a type of a base included in the consensus sequence is determined, if a type of a base indicated by a base sequence of a first fragment among the fragment base sequences is different from that indicated by a base sequence of a second fragment among the fragment base sequences, a symbol indicating either of the two bases may be used for the base.

A storage medium according to the present invention is intended to store a program for making a computer execute the above described method according to the present invention. As the storage medium, a floppy disk, any type of ROM, a hard disk, a mini disk, or a RAM may be used.

BRIEF DESCRIPTION OF THE DRAWINGS

FIG. 6 is a schematic diagram showing a method for storing trace data;

FIG. 7 is a schematic diagram showing a method for storing original base sequence data;

DESCRIPTION OF THE PREFERRED EMBODIMENT

Figure 1:
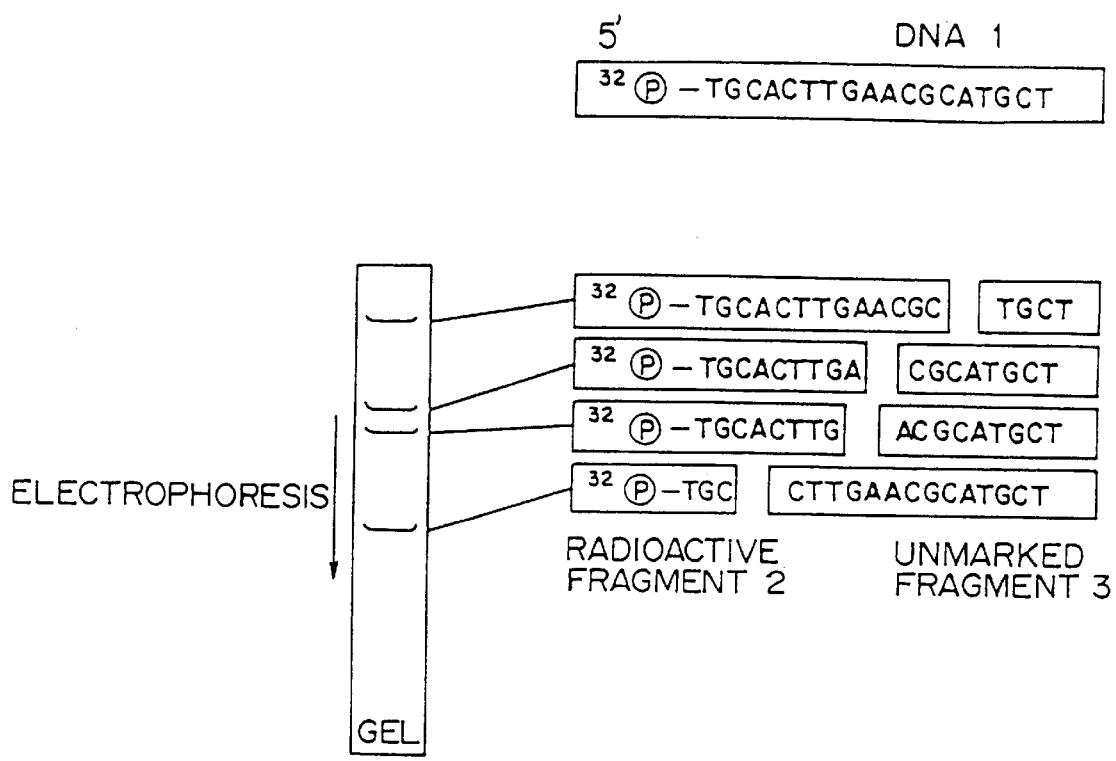
FIG. 1 is a schematic diagram showing a process for generating DNA fragments.
Figure 2:
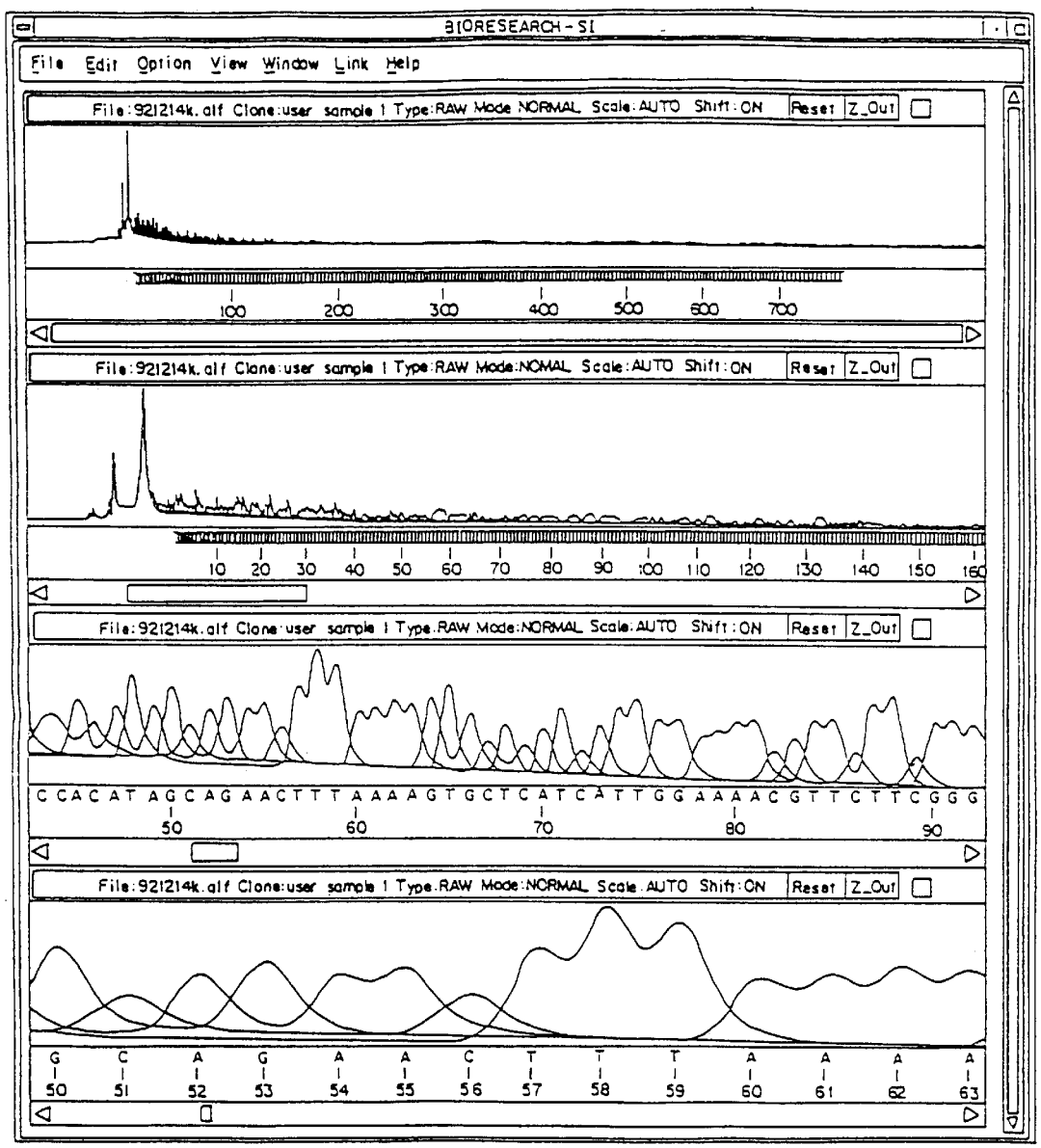
FIG. 2 shows an example of traces obtained by a sequencer.
Figure 3:
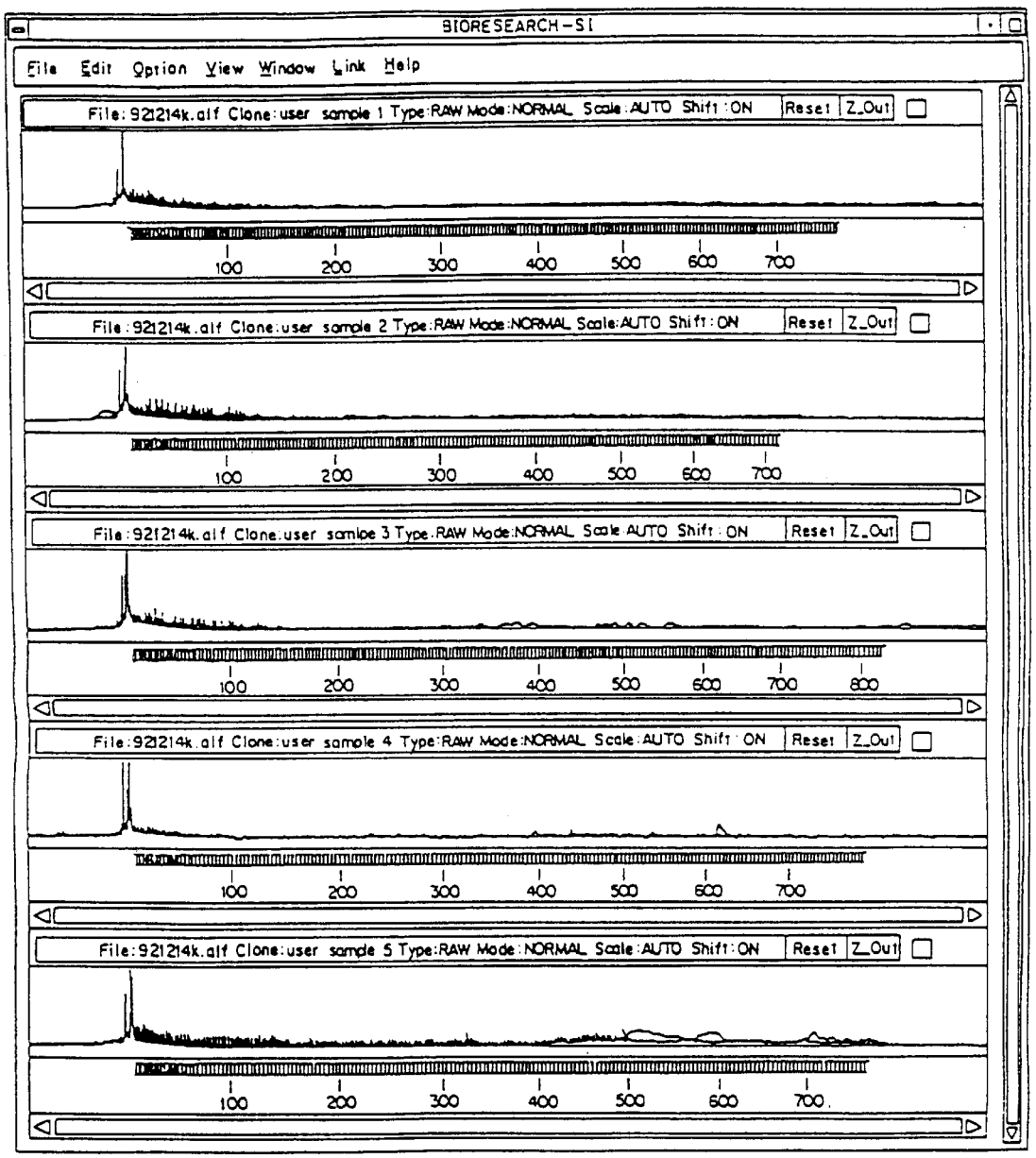
FIG. 3 shows an example of a graph where base intervals are uneven.
Figure 4:
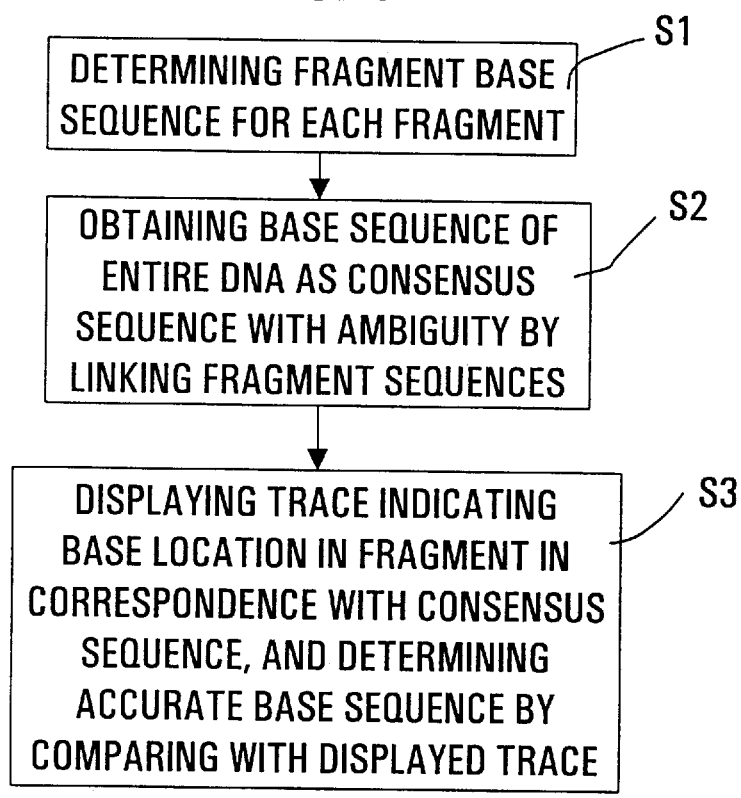
FIG. 4 is a block diagram showing a fundamental process according to the present invention.

FIG. 4 is a block diagram showing a fundamental process of a method according to the present invention. The method according to the present invention is a fragment trace data display method used to determine a base sequence of an entire DNA by separating the base sequence of the DNA into a plurality of fragments, displaying a trace (waveform) indicating locations of bases included in each of the plurality of fragments, and linking and editing base sequences corresponding to a plurality of traces.

With the fragment trace data display method as shown in FIG. 4, a base sequence of each fragment is first determined as a fragment base sequence in step S1. The fragment base sequence is obtained by, for example, an output from a DNA sequencer used for determining a base sequence of a DNA.

In step S2, fragment base sequences determined in step S1 are linked, so that one consensus sequence indicating the base sequence of the entire DNA, or a base sequence resulting from linkage of a plurality of fragments, is obtained. For the consensus sequence, ambiguity, such as indicating that a base at a certain location is either of two bases, determining the base sequence using a mark which does not designate a particular base, etc., is allowed.

In step S3, a trace indicating the locations of bases included in each of the fragment base sequences is displayed in correspondence with the consensus sequence, and an editing operation such as removing an unsuitable base, inserting a base depending on need, etc. is performed based on a comparison between displayed traces, so that the base sequence of the entire DNA with the ambiguity removed is determined.

With this process, the trace display facilitating the editing operation by comparing the displayed traces is performed in correspondence with the consensus sequence. The display method is, for example, like the one described below.

Location information indicating a location on a trace is provided to each of the bases included in a fragment base sequence output from a DNA sequencer. However, such location information is not provided to a base inserted into the fragment base sequence during editing. Bases positioned at both ends of the fragment base sequence among bases having the location information included in the fragment base sequence being edited, are identified, so that a corresponding trace is, for example, scale-converted and displayed in correspondence with the consensus sequence.

By performing such a trace data (waveform data) display operation, a relationship between a consensus sequence being edited and an original trace can be determined with ease, thereby identifying a correct DNA base sequence quickly.

Figure 5:
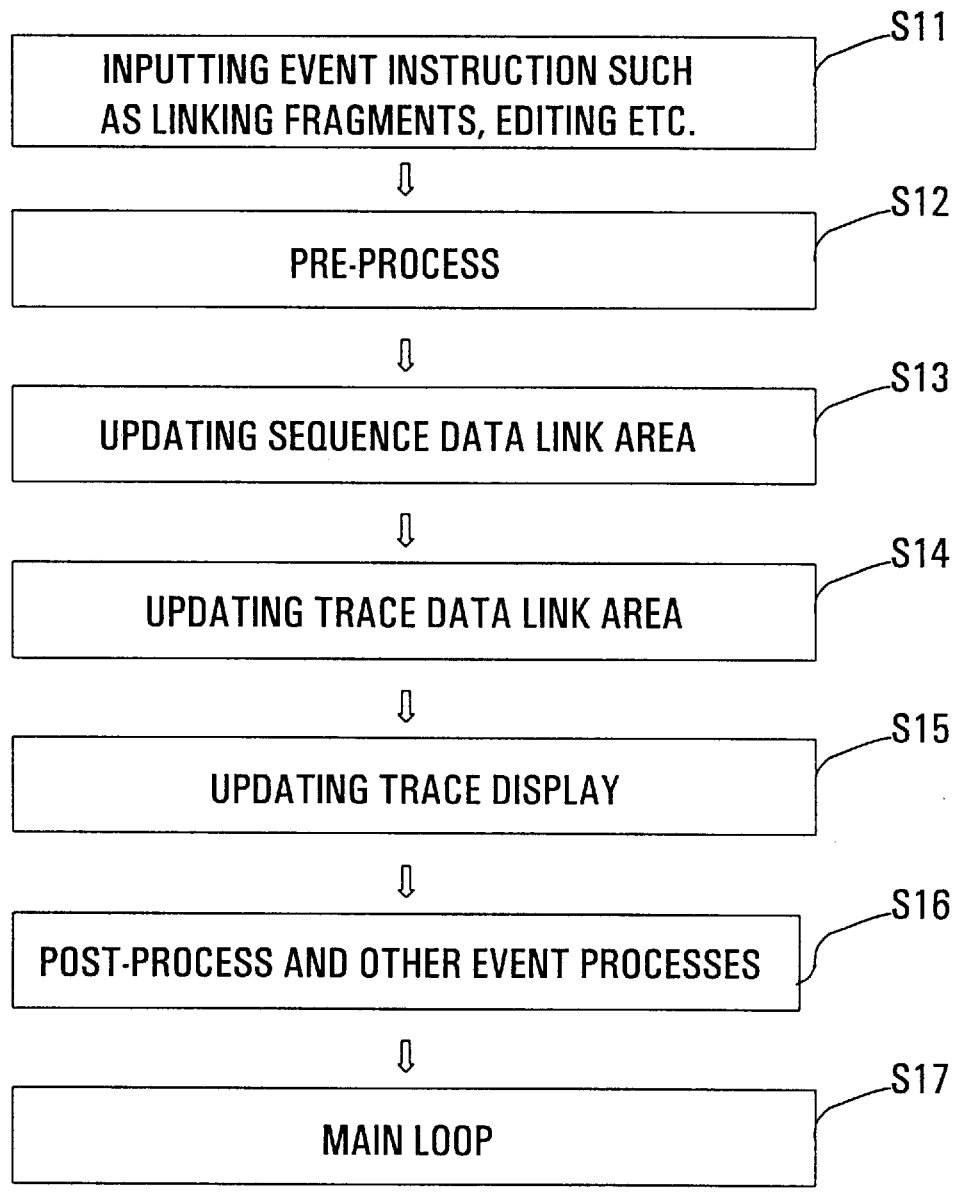
FIG. 5 is a flowchart showing a process for linking and editing base sequences using a trace data display method according to the present invention.

FIG. 5 is a flowchart showing an entire process for linking and editing base sequences using the wave display method according to this embodiment. The flowchart shown in this figure shows a trace data display process from a start, till an update performed each time an event such as linking fragments, performing an editing operation, etc. is executed.

In FIG. 5, an instruction of an event such as linking fragments, performing an editing operation, etc. is input in step S11. Then, a pre-process such as linking the fragments, rewriting a base sequence, etc. is performed depending on need in step S12. Steps S1 and S2 shown in FIG. 4 may be included in this step.

Next, a sequence data link area is updated in step S13. The sequence data link area indicates a partial area of a base sequence between bases respectively having corresponding trace data closest to the start and the end (both ends may be included), among bases in a fragment base sequence being edited.

For a base included in a base sequence obtained as an output from a DNA sequencer, its location on trace data, that is, corresponding location information, can be known as will be described later. Therefore, such base data is stored, for example, in a memory in correspondence with the location information. In the meantime, for a base such as the one inserted during editing, corresponding location information is not stored. This is because a corresponding location on the trace data is unknown. Accordingly, the sequence data link area indicates an area between the leftmost and rightmost bases respectively, having corresponding location information in the fragment base sequence (both ends may be included).

In FIG. 5, after the sequence data link area is updated and a sequence data link area corresponding to the fragment base sequence is obtained in step S13, a trace data link area is updated in step S14. The trace data link area is an area between locations indicated by trace data location information possessed by the bases positioned at both ends of the above described sequence data link area, that is, a partial area of trace data between locations of the leftmost and rightmost bases. With the update process performed in this step, a trace data link area corresponding to the sequence data link area in the fragment base sequence to be edited, is obtained.

After the trace data link area corresponding to the sequence data link area to be edited is obtained, a trace display is updated (to be described later) in step S15. Then, a required post-process and other event processes are performed in step S16. In step S17, a main loop process for displaying an actual trace is performed.

Provided next is the explanation about the concept of a consensus sequence according to the present invention. To determine a base sequence of a very long DNA chain as described above, the DNA is separated into a plurality of fragments. After a base sequence in each of the plurality of fragments is determined using a DNA sequencer, the base sequence of the entire DNA is determined by linking and editing the base sequences of the plurality of fragments. One base sequence produced in a process for linking base sequences of a plurality of fragments in order to determine a base sequence of an entire DNA, is called a consensus sequence. An example of the consensus sequence is provided below. Note that this example shows only one of the double chains.

| base number | 1 | 5 | 10 | 15 | 20 | 25 |
|---|---|---|---|---|---|---|
| consensus sequence | ATGCTTAGSWGTACCARGGTAAAAA | | | | | |

| | -continued |
|---|---|
| fragment A | ATGCTTAGCTGTACCAG |
| fragment B | TTAGGT-TACCAAGGTA |
| fragment C | AGCAGTACCAAGGTAAAAA |

This example shows a consensus sequence generated by linking three fragments A, B, and C. If overlapped bases are identical in overlapped portions of the fragments, they are used as bases in the consensus sequence as they are. If the overlapped bases are different, they are represented by an IUPAC code. That is, if a base in the overlapped portions is considered to be either of C and G, it is replaced with "S" (corresponding to the above described base number 9). If the base is considered to be either of T and A, it is replaced with "W" (corresponding to the base number 10). If the base is considered to be either of G and A, it is replaced with "R" (corresponding to the base number 17). By performing these replacements, the consensus sequence is obtained.

Provided next is the explanation about a structure of the data used for the trace data display method according to the present invention. As the data used by the trace data display method according to the present invention, consensus data set for each consensus sequence can be generated. The consensus data includes "Fragment Cnt" indicating a fragment number (the number of fragments) belonging to the consensus sequence, a pointer "pFragment [Fragment Cnt]" pointing to information specific to a fragment belonging to the consensus sequence (to be described later), and a "Consensus [Consensus Cnt]" indicating a base sequence of the consensus sequence.

Provided next is the explanation about fragment data used by the trace data display method. The fragment data includes trace data, original base sequence data, base sequence data for editing, base data for editing, and fragment-specific information.

The trace data includes trace data of each of the four bases, that is, adenine A, thymine T, guanine G, and cytosine C. Data obtained by performing approximately 10,000 samplings at predetermined intervals, is stored as each trace data of each of the bases. At this time, the trace data has a two-dimensional sequence. That is, at 10,000 data points represented by a data point location "x", data such as 16-bit data indicating a height of each trace is stored. Here, each trace data is represented as follows:

WaveData [0] [x]: trace data of A (adenine)
    WaveData [1] [x]: trace data of T (thymine)
    WaveData [2] [x]: trace data of G (guanine)
    WaveData [3] [x]: trace data of C (cytosine)
    x: data point location (wave data point)

The original base sequence data, which is obtained by a DNA sequencer, is a fragment base sequence before linking or editing. An example of the original base sequence data is provided in FIG. 7. As shown in this figure, the original base sequence data is represented by associating each of the bases included in an original fragment and its location with a base number "n" (the original base number "OriginalBaseNumber"). A base type is represented by a base code (BC) conforming to the IUPAC code, while a base location is represented by a wave data point, that is, the data point location "x" (data point location at a peak of a trace corresponding to each of the bases) shown in FIG. 6.

The original base sequence data is represented by an original base having the following symbol.

Originalbase [n−1]: original base (n: base number, $1 \leq n \leq$ [total number of original base sequences])

The base sequence data for editing is data representing a base sequence to be edited, composed of a number of a base being edited (m) and a pointer (P) pointing to base data for editing, to be described next. The base sequence data for editing is represented by an edit base having the following symbol.

pEditBase [m−1]: edit base (m: base number being edited, 1≦m≦[total number of bases in a base sequence being edited]

The base data for editing is data pointed to by a pointer of the base sequence data for editing, and includes a base code (BC) and an original base number "OriginalBaseNumber". The base code (BC) is a character indicating a base type, while the original base number "OriginalBaseNumber" is a number of a base "n" in an original base sequence indicated by the base code (BC). For a base which does not have a corresponding base in an original base sequence, such as the one inserted during editing, the original base number is defined as "−1".

Figure 8:
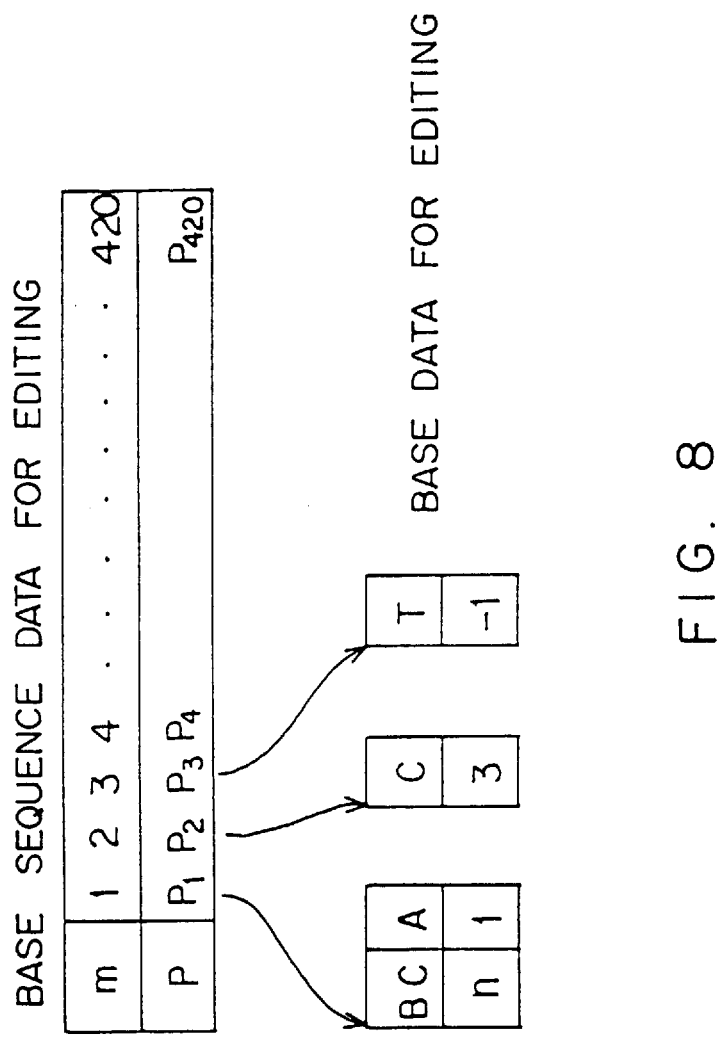
FIG. 8 is a schematic diagram showing a method for storing base sequence data for editing and base data for editing.

FIG. 8 shows both the base sequence data for editing and the base data for editing. The base sequence data for editing is a sequence of the pointer P pointing to base data for editing in correspondence with a base number, as described above. Since a base in a structure "T" pointed to by a pointer $P_3$ does not exist in original base sequence data which is the second data, the original base number of this base is The fragment-specific information is information specific to each fragment corresponding to trace data and sequence data. The fragment-specific information includes the following data.

pwave: pointer pointing to WaveData
pOriginalData: pointer pointing to OriginalBase
pEditData: pointer pointing to pEditBase
OffsetBase: first location of a fragment in a consensus sequence (offset base)
LeftBaseNumber: base number at a left end of sequence data link area in a base sequence for editing
RightBaseNumber: base number at a right end of a sequence data link area in trace data
LeftWaveDataPoint: location of a data point at left end of trace data link area in trace data
RightWaveDataPoint: location of a data point at right end of trace data link area in trace data The offset base "OffsetBase" indicates where the beginning (left end) of a base sequence of each fragment is positioned in a consensus sequence. In the above described example of the consensus sequence, the offset base of the fragment B is 5.

Figure 9:
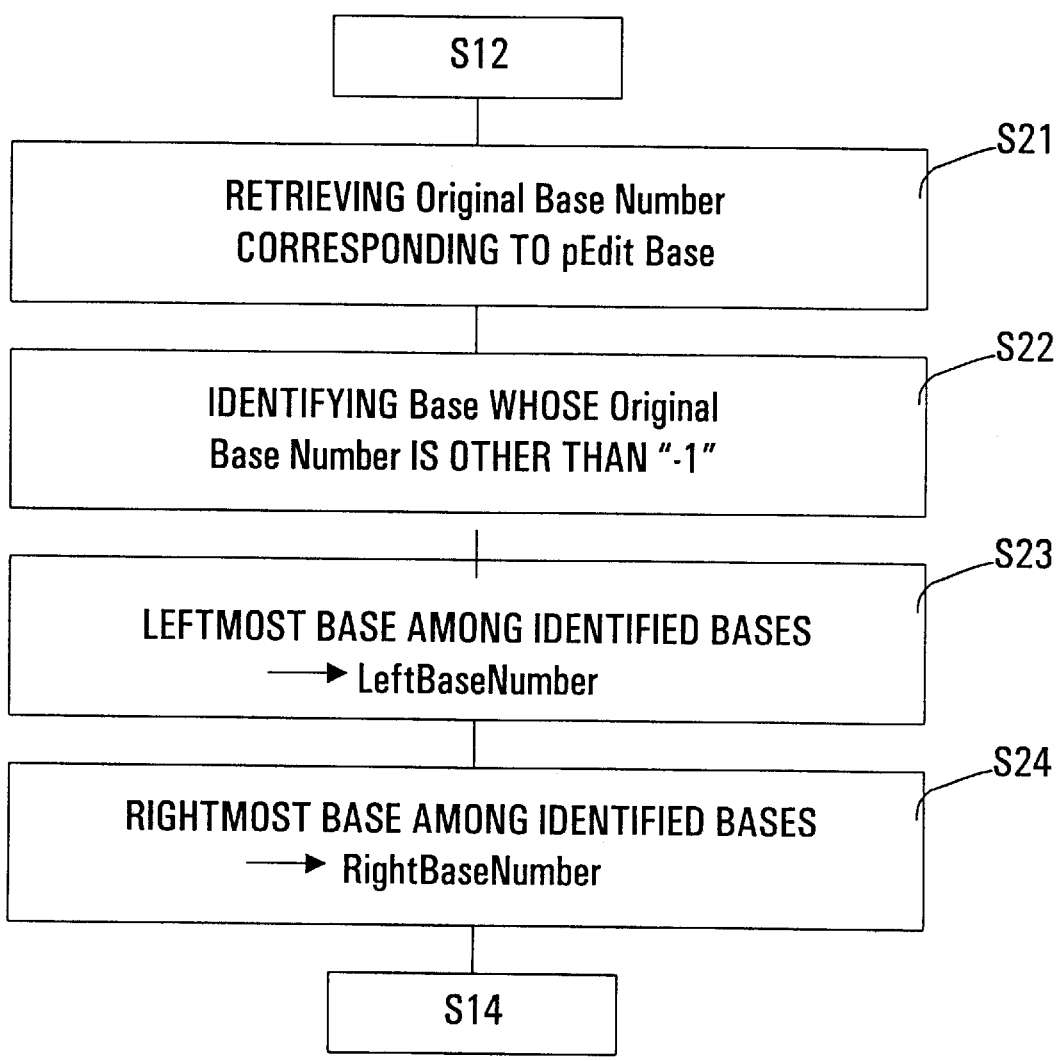
FIG. 9 is a flowchart showing a process for updating a sequence data link area.
Figure 10:
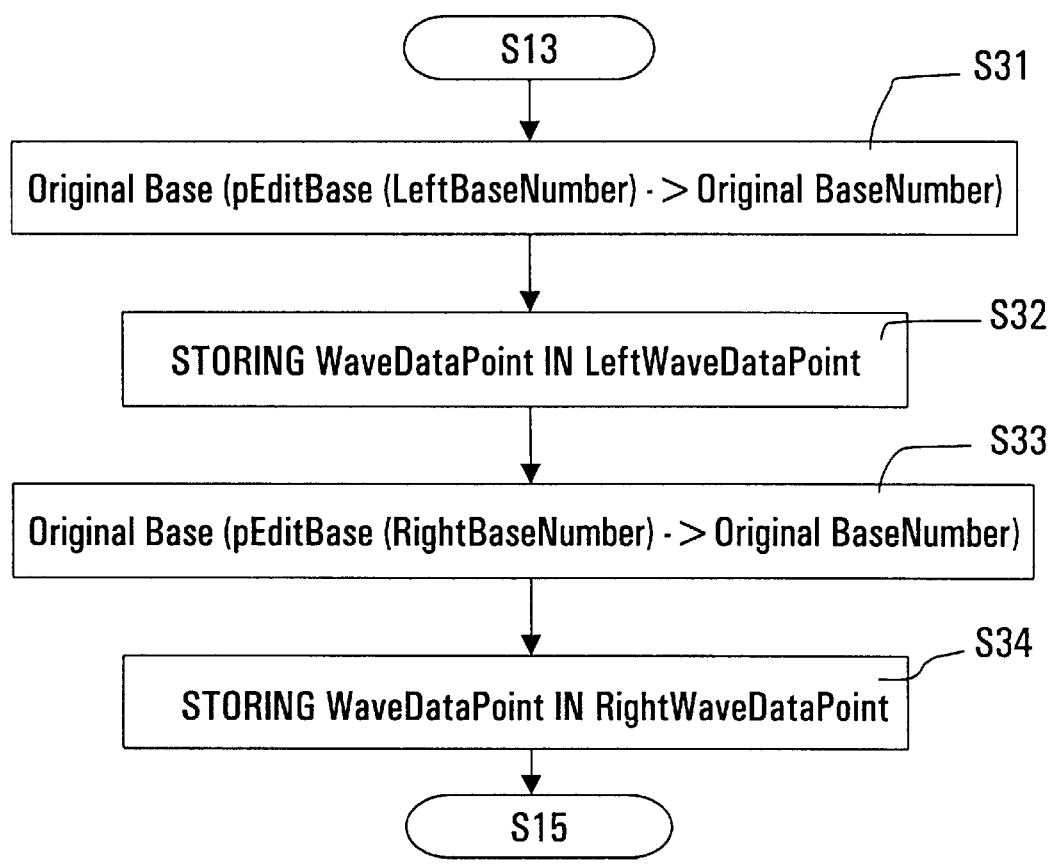
FIG. 10 is a flowchart showing a process for updating a trace data link area.
Figure 11:
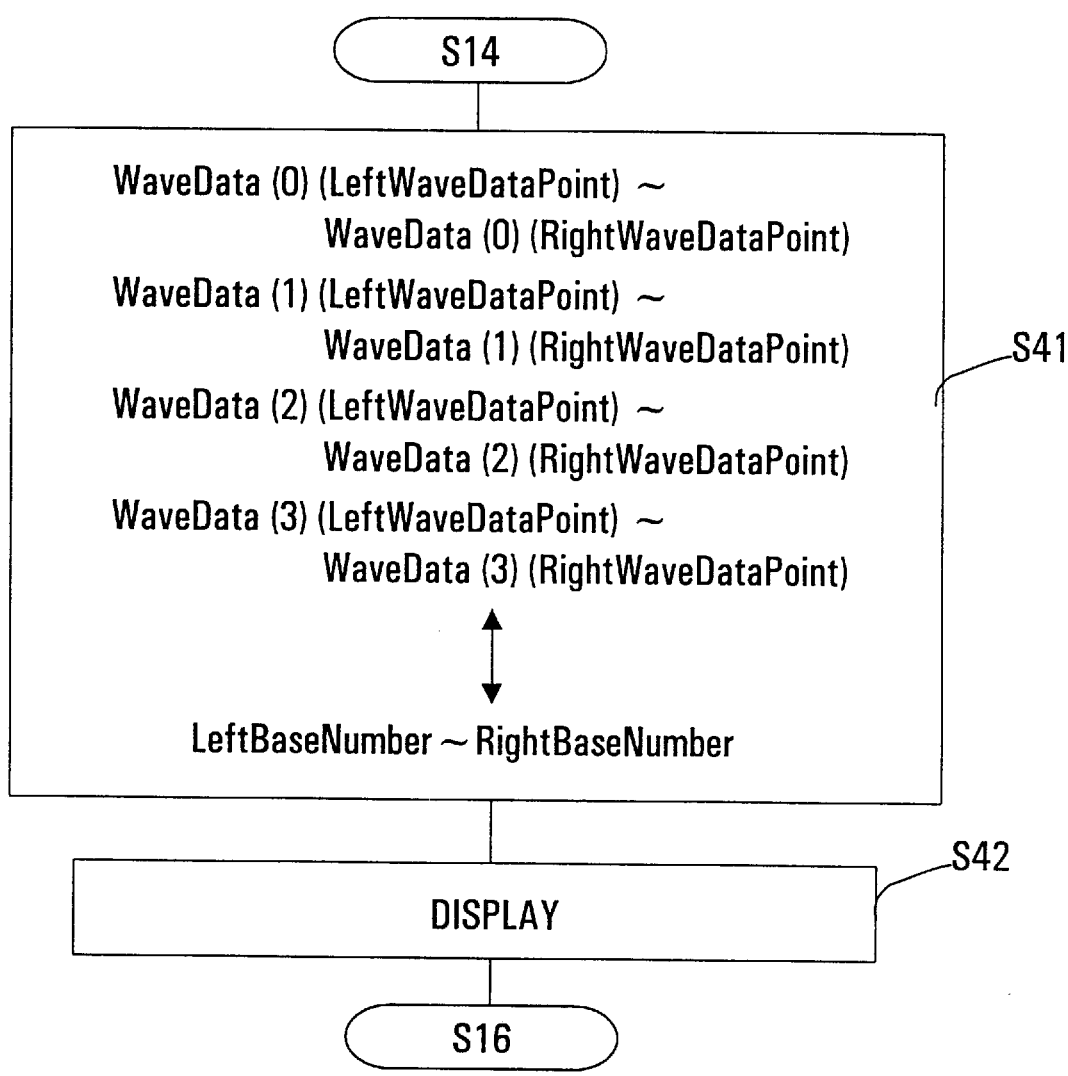
FIG. 11 is a flowchart showing a process for updating a trace data display.

Provided next is the detailed explanation about a process performed in steps S13 through S15 according to this embodiment, by referring to FIGS. 9 through 11.

FIG. 9 is a flowchart showing a process for updating a sequence data link area performed in step S13. In this figure, for all of the edit bases (pEditBases), that is, all of the bases included in the base sequence data for editing, the original base number "OriginalBaseNumber", which is a number of the base data for editing, is examined (step S21). A base whose original base number "OriginalBaseNumber" is not "−1" is identified (step S22). Base numbers of the leftmost and rightmost bases among identified bases are stored as a left base number "LeftBaseNumber" and a right base number "RightBaseNumber" respectively (steps S23 and 24).

FIG. 10 is a flowchart showing the process performed in step S14 of FIG. 5, that is, the process for updating a trace data link area. As shown in this figure, a location of an original base corresponding to the left base number "Left-BaseNumber" obtained in FIG. 9, that is, a wave data point "x" corresponding to a base number "n" of the same base in the original base sequence data, is obtained (step S31). The obtained wave data point is stored as the left wave data point "LeftWaveDataPoint") (step S32). Similarly, a location of an original base "x" corresponding to the right base number "RightBaseNumber" is obtained (step S33). A wave data point "WaveDataPoint" in the original base sequence data corresponding to the right base number "RightBaseNumber", is stored as a right wave data point "RightWaveDataPoint". (step S34).

FIG. 11 is a flowchart showing the process performed in step S15 of FIG. 5, that is, the process for updating a trace display. In this step, scale conversion is performed for four sets of trace data "WaveData" respectively corresponding to the four bases, so that a trace between the left wave data point "LeftWaveDataPoint" and the right wave data point "RightWaveDataPoint" corresponds to a portion between the left base number "LeftBaseNumber" and the right base number "RightBaseNumber", in a consensus sequence, when displayed (step S41). The trace after the scale conversion is then displayed (step S42).

That is, according to the present invention, a trace corresponding to each fragment is scale-converted and displayed at a location corresponding to a consensus sequence. Each time any change is made to a location of a base in a fragment base sequence or its contents due to a process such as an editing process, etc., the location of the trace data is scale-converted and displayed.

Assume that the number of bases included in a fragment base sequence is changed from 345 to 350 due to an editing process, etc., and this fragment base sequence ranges from a 101st base to a 450th base in a consensus sequence. In this case, the scale conversion and a shift of display location, etc. are performed, so that the first base of the fragment base sequence is moved to the 101st location, and the 350th base originally positioned at the 345th location is moved to the 450th location. Then, a trace after editing is displayed. That is, when the number of bases is changed to "n+5" by an operation such as a linking operation or an editing operation for a fragment whose number of bases is determined to be "n" by a DNA sequencer, a trace corresponding to the sequence composed of "n" bases determined by the DNA sequencer is displayed in a range of "n+5" bases.

According to the present invention, a distortion correction for automatically correcting the distortion of a distance travelled by a gel electrophoresis is made to equalize base intervals corresponding to a trace, thereby facilitating a simple comparison between traces. The method for making the distortion correction is described below.

When a molecule with a molecular weight equal to or less than 300,000 is electrophoresed in a gel, it is experimentally proved that the following equation between the travelling speed of the molecule and the molecular weight is approximately satisfied.

$$v = -C_1 \cdot \log m + C_2 \qquad (1)$$

(m: molecular weight>0, v: moving speed>0, $C_1$: constant>0, $C_2$: constant>0)

The measurement of fluorescence intensity is performed at predetermined intervals ($T_1$>0) set for each experiment. Assuming that a predetermined distance between a location at which the electrophoresis starts and a location at which the fluorescence intensity is detected, is $C_3$>0

$$C_3 = v(T_1 x + T_2) \qquad (2)$$

(x=the number of data points from the first detected base)

($T_2$: the amount of time from the electrophoresis start till the detection of the first (x=0) base>0)

This embodiment is based on the assumption that the trace display data does not include data immediately after the start of electrophoresis. That is, data of the fluorescence intensity starts to be captured after a predetermined amount of time elapses from the start of electrophoresis. To take advantage of the equation (1), a distance between the location at which the electrophoresis starts, that is, the location at which a sample is injected, to the location at which the fluorescence intensity is detected, must be obtained. This distance is represented by the equation (2). $T_2$ in the equation (2) is an amount of time from the start of electrophoresis, that is, a time point at which a voltage is applied, till a time point at which the fluorescence intensity starts to be captured as data. The data of the fluorescence intensity is measured at predetermined intervals ($T_1$)—normally at one-second intervals, and "x" indicates the number of data points. "v" in the equation (2) indicates an electrophoresis speed of a DNA base measured as "xth" data. Note that the start of electrophoresis means a time point at which a voltage is applied to an electrophoresis device, and the fluorescent intensity is measured from the time point at which the electrophoresis starts, but its data is started to be kept after a predetermined amount of time elapses.

By using the equations (1) and (2), an equation for associating the number of data points "x" whose base intervals are corrected to be even (regular) with the base number "n", is defined as follows.

First of all, from both of the equations (1) and (2)

$$C_3/(T_1 x + T_2) = -C_1 \log m + C_2 \log m = -C_3/C_1(T_1 x + T_2) + C_2/C_1 \quad (3)$$

Assuming $$C_4 = C_3/C_1 > 0, \ C_5 = C_2/C_1 > 0$$

the equation (3) is therefore, $$\log m = -C_4/(T_1 x + T_2) + C_5 \quad (4)$$

Also assuming that a molecular weight of a primer is $M_P$, the base number is n, and an average molecular weight of bases is $M_B$, $$m = M_P + (n-1) M_B \quad (5)$$

can be obtained.

If the equation (5) is assigned to the equation (4), $$\log \{M^P + (n-1) M_B\} = -C_4/(T_1 x + T_2) + C_5$$
$$M_P + (n-1) M_B = 10^{\{-C_4/T_1 x + T_2) + C_5\}}$$
$$\therefore n = f(x)$$
$$= [10^{\{-C_4/(T_1 x + T_2) + C_5\}} - M_P]/M_B + 1 \quad \ldots (6)$$

where $M_P$ is defined as a molecular weight of a primer for each sequencing.

For $M_B$, an average molecular weight of bases 316 is used. As $T_1$, a measurement interval set in sequencing is used. As $T_2$, an amount of time from the start of electrophoresis till the detection of the first (n=0) base is used.

For a trace display, the constants $C_4$ and $C_5$ in the equation (6) are determined from the corresponding actual electrophoresis data to be used.

For this determination, RightBaseNumber and LeftBaseNumber are used. That is, if n=RightBaseNumber, x=x [RightBaseNumber]. Or, if n=LeftBaseNumber, x=x [LeftBaseNumber]. Therefore, by assigning these equations to the equation (6), the constants $C_4$ and $C_5$ are determined for each fragment.

Normally, "x" is defined as a horizontal axis for a trace display, but here "n" is defined as the horizontal axis. The scale conversion is performed by using trace data corresponding to "n", which ranges from LeftBaseNumber to RightBaseNumber, and its result is displayed.

Figure 6:
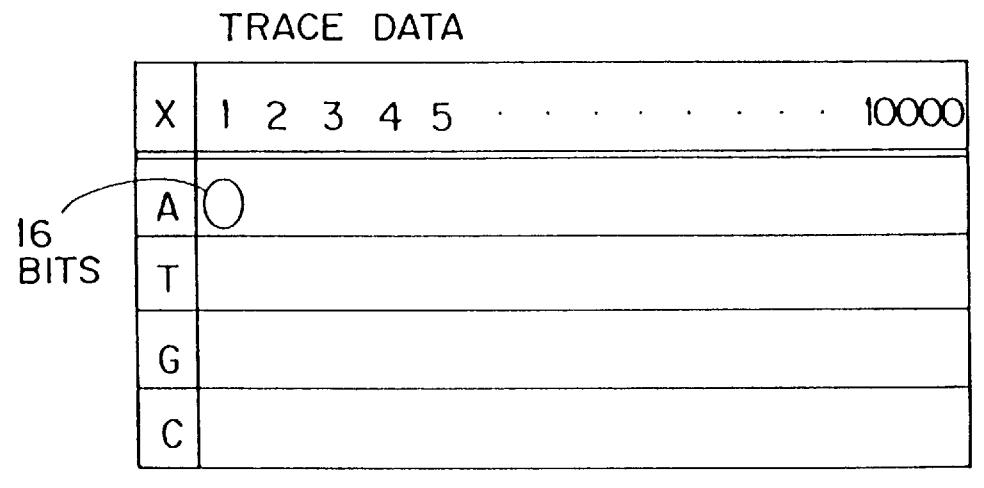

As described above, a sequence of trace data whose base intervals are corrected to be approximately regular, is obtained based on the equation (6). Its result is stored, for example, in a memory, and used for displaying a trace. The data shown in FIGS. 6 and 7 are updated according to the result of this calculation, while the data shown in FIG. 8 is not updated.

Figure 12:
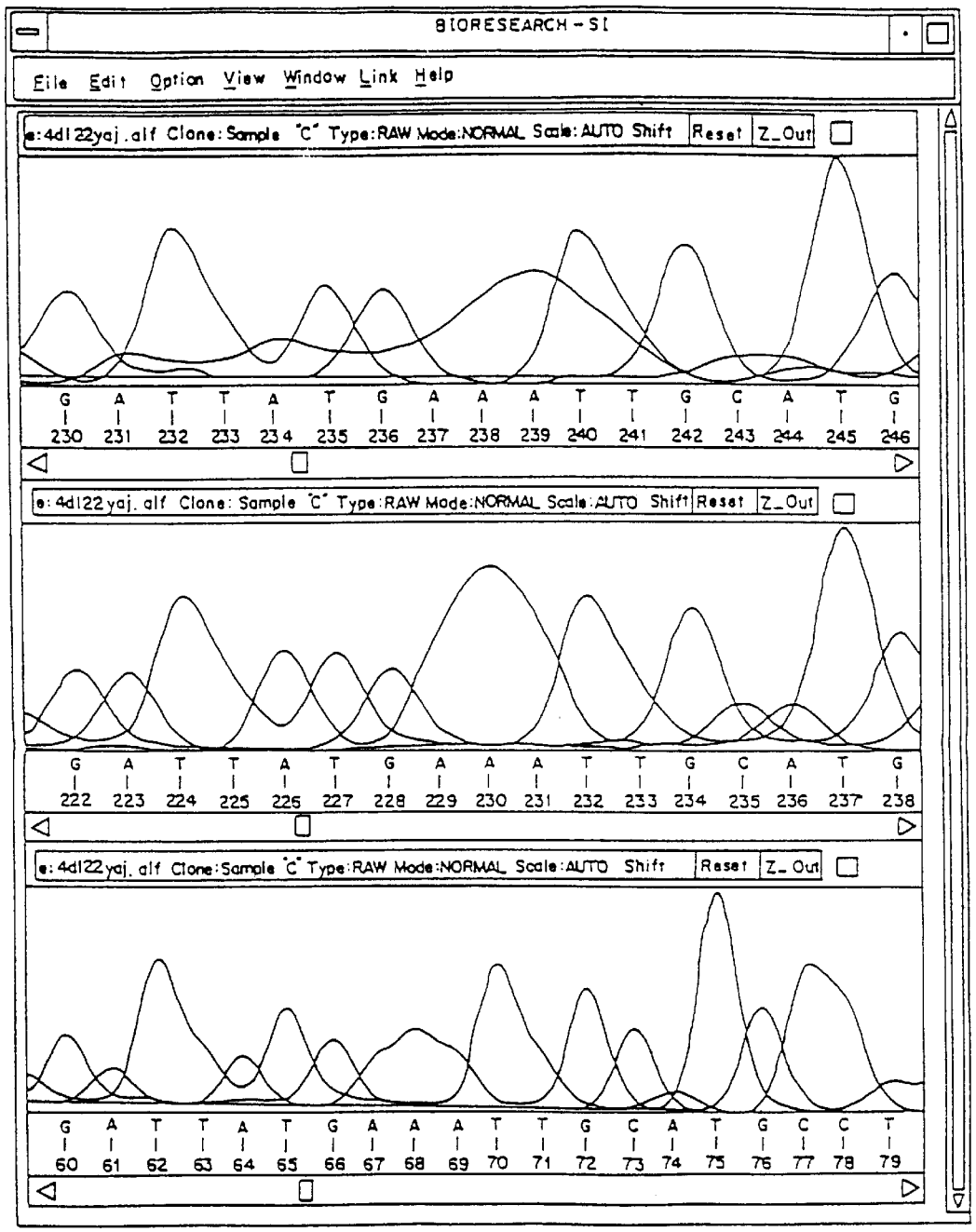
FIG. 12 shows traces output from a DNA sequencer (before scale conversion)
Figure 13:
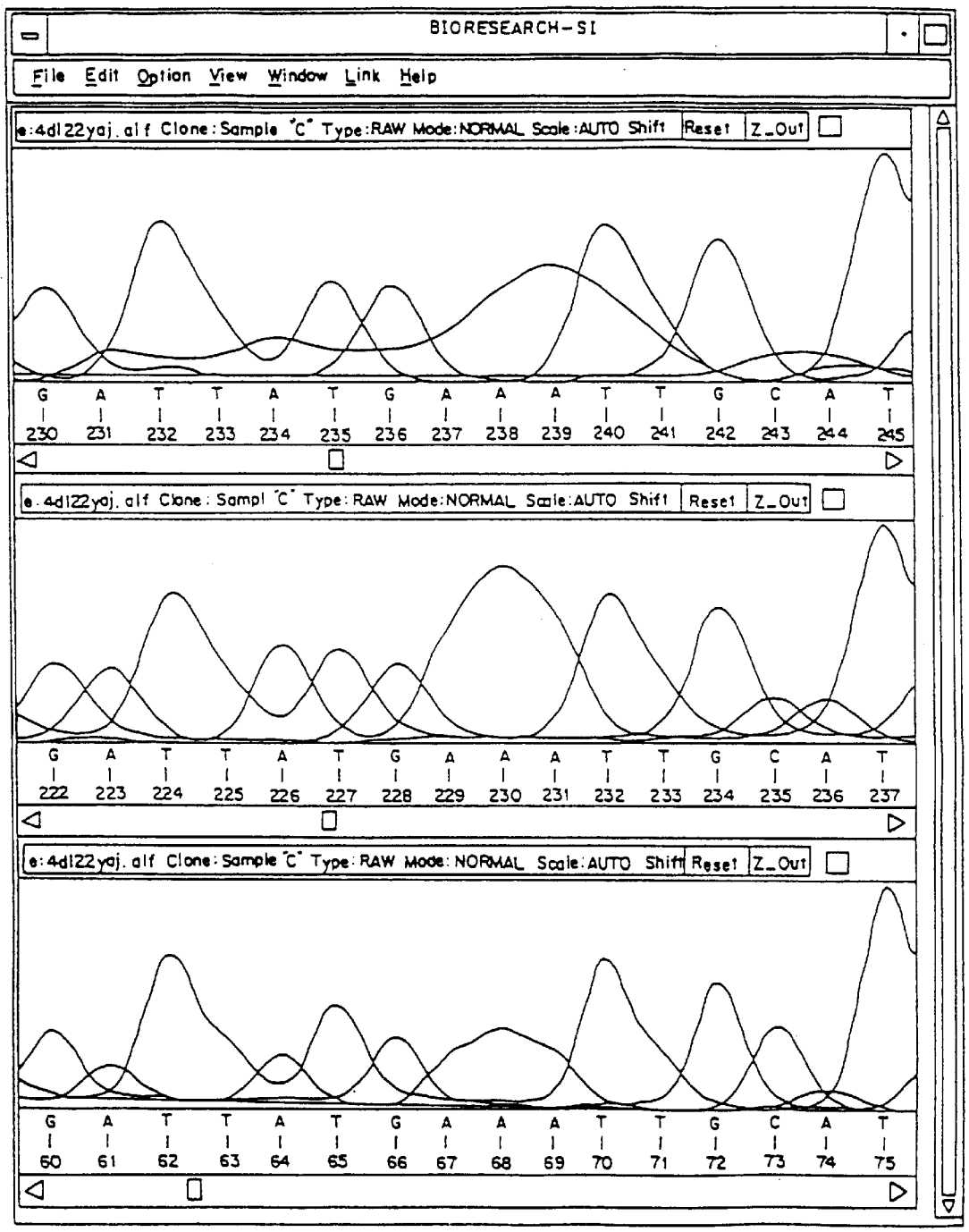
FIG. 13 shows a result obtained by applying the trace data display method according to the present invention to the traces shown in FIG. 12 (after the scale conversion)

FIGS. 12 and 13 are schematic diagrams showing a fragment trace display varying due to the above described editing process. FIG. 12 shows an output from a DNA sequencer as it is, while FIG. 13 shows a result of using the trace data display method according to the present invention. It is understood from the figure that the base intervals of the lowest traces are regular in comparison with the upper traces.

Figure 14:
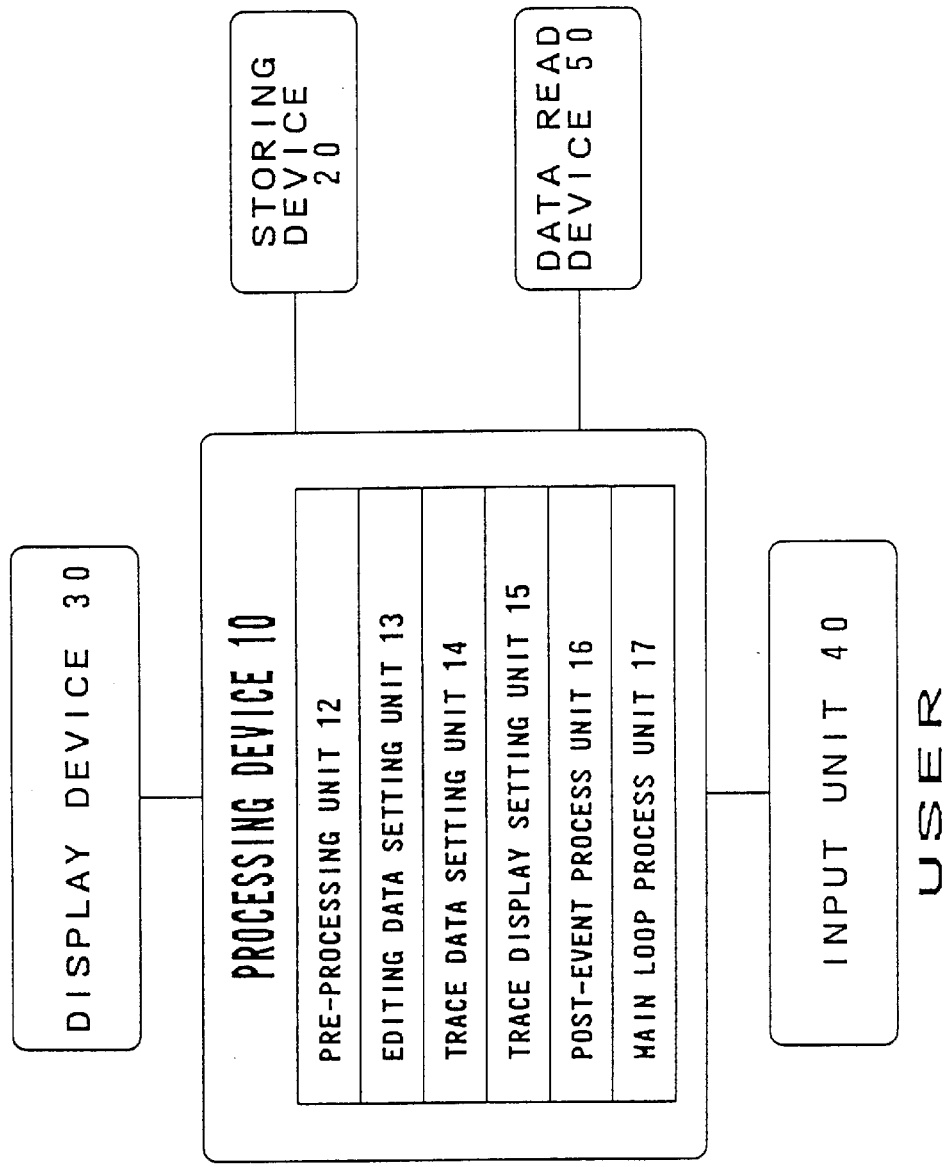
FIG. 14 is a block diagram showing the configuration of a trace data display device according to the present invention.

The above described method according to the present invention can be implemented, for example, by a control device employing a computer. As shown in FIG. 14, the control device comprises a processing device 10, a storing device 20, a display device 30, an input unit 40, and a data read device 50.

The processing device 10 comprises a pre-process unit 12 for performing the pre-process in step S12 of FIG. 5, an editing data setting unit 13 for performing the process for updating a sequence data link area in step S13, a trace data setting unit 14 for performing the process for updating a trace data link area in step S14, a trace data display unit 15 for performing the process for updating a trace display in step S15, a post-event process unit 16 for performing a post-process and other event processes in step S16, and a main loop process unit 17 for performing the main loop process in step S17. Note that the processing device 10 may include any of the units for performing processes in respective steps of FIGS. 4, 5, and 9 through 11 among the steps of the method according to this embodiment.

The storing device 20 stores a program used for performing the above described processes, data used for each of the processes, and data created or updated by each of the processes. A hard disk, a RAM, a ROM, or an information storing unit of various types, may be employed as the storing device 20. These program and data may be stored in an external storage medium. They may be input/output to/from the processing device 10 via the data read device 50. A magnetic disk, an optical disk, a magneto-optical disk, and other storage media may be employed as the external storage medium.

The display device 30 is used to display a graph representing a base sequence and a base trace in the processes of the present invention as shown in FIGS. 12 and 13. The display unit 30 is also used to display a menu for selecting a program used for executing the method according to the present invention, and to select data of various types. A user may select the program and the data of various types via the input unit 40.

Figure 15:
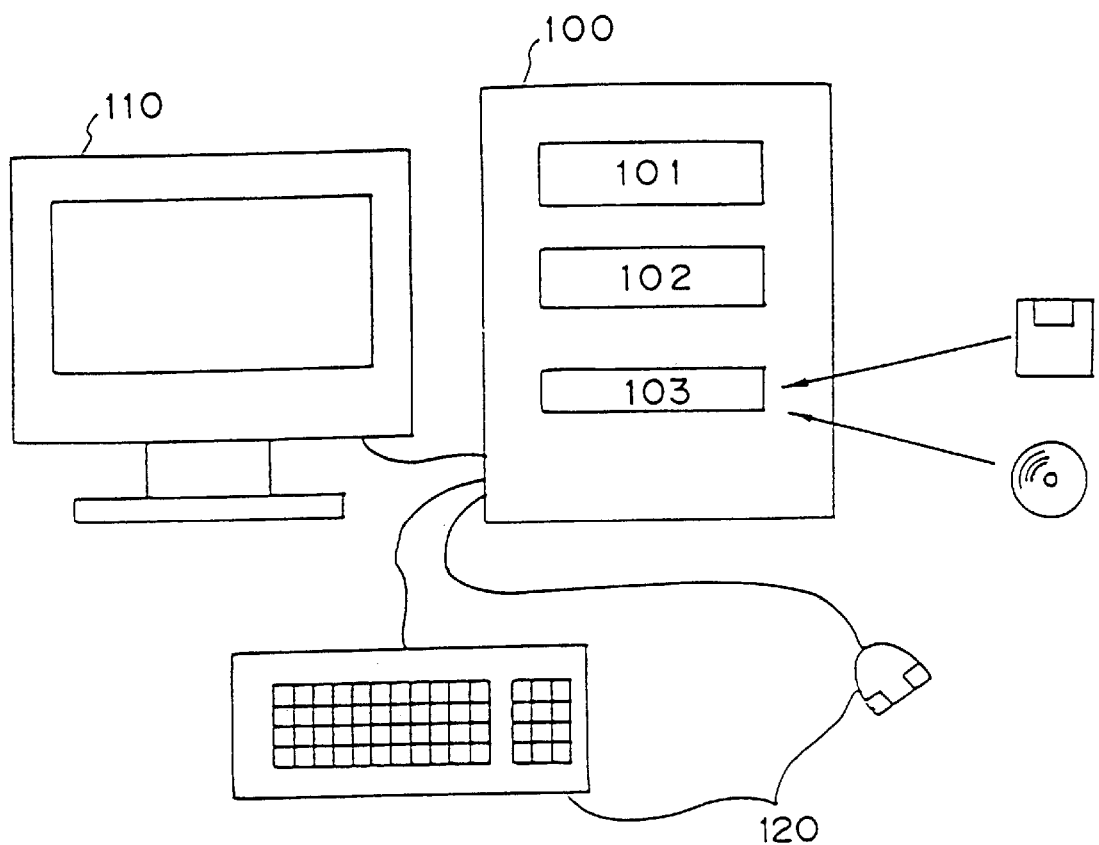
FIG. 15 is a schematic diagram showing a computer system for implementing the present invention.

FIG. 15 is a schematic diagram showing a computer system for implementing the present invention. By programming the method according to the present invention, and making the computer system execute the method, the system can be used as a processing device according to the present invention.

This computer system comprises a computer 100, a display device 110, and an input device 120. The computer 100 comprises a processing device 101, a memory 102, and a driver for a storage medium 103. The input device comprises a keyboard and a mouse.

The processing device 101, which corresponds to the processing device 10 shown in FIG. 14, performs each of the programmed processes in this embodiment. The memory 102, which corresponds to the storing device 20 shown in FIG. 14, stores a program for performing each of the processes, data used for each of the processes, and data and files required for other processes. The processes according to the present invention may be programmed and stored in a storage medium. The driver 103 is intended to read a program stored in such a storage medium, and corresponds to the data read device 50 shown in FIG. 14. An optical medium, a magnetic medium, and a magneto-optical medium such as a floppy disk, a CD-ROM, an MD, etc. may be employed as the storage medium.

The display device 110, which corresponds to the display device 30 shown in FIG. 14, displays a graph created during, or as a result of, a process of the present invention. The input device 120 is used by a user in order to give instructions for performing a process of the present invention to a computer system.

According to the present invention as described above in detail, a trace can be displayed, compared and studied in real time in correspondence with a linkage or editing state of fragments, for example, simultaneously with an editing operation. As a result, a base sequence can be determined while visually verifying the accuracy of a result of linkage or editing process. Additionally, since the linkage and the editing can be performed while verifying the consistency of the trace data, as well as the consistency in a character sequence as a base symbol sequence, the base sequence can be assembled more accurately and more quickly. Furthermore, base intervals corresponding to traces can be made even, thereby facilitating a comparison between traces. As a result, sequencing mistakes can be prevented.

a portion of the DNA and traces representing the base sequences of the plurality of fragments, which are obtained by a DNA sequencer, comprising:

pre-process means for determining a consensus sequence by linking the base sequences of the plurality of fragments of the DNA obtained by the DNA sequencer;

editing data setting means for determining a base sequence to be edited in the consensus sequence;

trace data setting means for identifying a trace corresponding to the base sequence to be edited among traces obtained by the DNA sequencer; and trace data display means for displaying the identified trace in correspondence with the base sequence to be edited, wherein bases in the base sequence to be edited are displayed spaced uniformly and wherein the trace is displayed from trace data corresponding to the uniformly spaced bases.

2. The device as set forth in claim 1, wherein:

the pre-process means provides location data indicating a corresponding location on the trace for each of bases included in the base sequences of the plurality of fragments of the DNA;

the editing data setting means identifies bases included in the base sequence to be edited, having the location information, and positioned at both ends of the base sequence to be edited; and the trace data display means displays a trace existing between the location data of the identified bases positioned at both ends in correspondence with the consensus sequence.

3. The device as set forth in claim 1, wherein:

the trace data display means displays the consensus sequence in correspondence with a displayed trace, so that an interval between contiguous bases becomes regular.

4. The device as set forth in claim 1, wherein:

when a type of a base included in the consensus sequence is determined, if the type of the base indicated by a base

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

C C A T A A A T A A   C C T T T                                  1 5

What is claimed is:

1. A device for determining a base sequence of a DNA based on base sequences of a plurality of fragments forming sequence of a first fragment among the fragment base sequences is different from the type of the base indicated by a base sequence of a second fragment among the fragment base sequences, a symbol indicating either of two bases is used for the base.

5. A storage medium readable by a computer, tangibly embodying a program on instructions executable by the computer to perform method steps for determining a base sequence of a DNA based on a base sequences of a plurality of fragments forming a portion of the DNA, and traces representing the base sequences of the plurality of fragments, the method steps comprising:

determining a consensus sequence by linking the base sequences of the plurality of DNA fragments obtained by the DNA sequencer;

determining a base sequence to be edited in the consensus sequence;

identifying a trace corresponding to the base sequence to be edited among traces obtained by the DNA sequencer; and displaying the identified trace in correspondence with the base sequence to be edited, wherein bases in the base sequence to be edited are displayed spaced uniformly and wherein the trace is displayed from trace data corresponding to the uniformly spaced bases.

6. The storage medium as set forth in claim 5, said method steps further comprising:

providing location data indicating a corresponding location on a trace for each of bases included in the base sequences of the plurality of DNA fragments;

identifying bases included in the base sequence to be edited, having location information, and being positioned at both ends of the base sequence to be edited; and displaying a trace existing between the identified bases at both ends in correspondence with the consensus sequence.

7. The storage medium as set forth in claim 5, wherein the method steps further comprising:

displaying the consensus sequence in correspondence with a displayed trace, so that an interval between contiguous bases becomes regular.

8. The storage medium as set forth in claim 5, wherein:

when a type of a base included in the consensus sequence is determined, if the type of the base indicated by a base sequence of a first fragment among the fragment base sequences is different from a type of the base indicated by a base sequence of a second fragment among the fragment base sequences, a symbol indicating either of two bases is used for the base.

* * * * *